US007216721B2

(12) United States Patent
Jacobson et al.

(10) Patent No.: US 7,216,721 B2
(45) Date of Patent: May 15, 2007

(54) FIRE EXTINGUISHER UNIT

(75) Inventors: Richard A. Jacobson, Philadelphia, PA (US); Brian K. Weller, Berwyn, PA (US)

(73) Assignee: EMC Packaging, Inc., Lakewood, NJ (US)

( * ) Notice: Subject to any disclaimer, the term of this patent is extended or adjusted under 35 U.S.C. 154(b) by 108 days.

(21) Appl. No.: 10/919,188

(22) Filed: Aug. 16, 2004

(65) Prior Publication Data

US 2006/0032642 A1 Feb. 16, 2006

(51) Int. Cl.

| | |
|---|---|
| ***A62C 8/00*** | (2006.01) |
| ***A62C 13/62*** | (2006.01) |
| ***A62C 31/02*** | (2006.01) |
| ***A61M 11/02*** | (2006.01) |

(52) U.S. Cl. ............................ 169/30; 169/71; 169/73; 169/75; 169/44; 239/302; 239/373; 239/375

(58) Field of Classification Search ................. 169/30, 169/71, 73, 75, 85, 44; 239/302, 373, 375, 239/378; 248/316.1, 154, 311.2

See application file for complete search history.

(56) References Cited

U.S. PATENT DOCUMENTS

| | | | | | |
|---|---|---|---|---|---|
| 3,565,384 | A | * | 2/1971 | Lockwood | 248/312 |
| 4,307,823 | A | * | 12/1981 | Heiss et al. | 222/633 |
| 5,664,700 | A | * | 9/1997 | Battle | 222/105 |
| 5,890,624 | A | * | 4/1999 | Klima et al. | 222/82 |
| 5,934,380 | A | * | 8/1999 | Finnerty et al. | 169/46 |
| 6,138,766 | A | * | 10/2000 | Finnerty et al. | 169/14 |

* cited by examiner

*Primary Examiner*—Davis Hwu
(74) *Attorney, Agent, or Firm*—Joseph M. Konieczny, Sr.

(57) ABSTRACT

A fire extinguisher unit that can be grasped and operated with a single hand. The unit includes a single-hand fire extinguisher and a holder for releasably supporting the fire extinguisher on a vertical surface. The fire extinguisher has a cylindrical canister housing, a flexible internal pouch containing fire suppressant, means for externally pressurizing the pouch, a valve for regulating the flow of fire suppressant from said pouch, and a spray head connected to the valve for actuating the valve between open and closed positions and for directing the flow of fire suppressant from said pouch. The holder has an elongate base, means for mounting the elongate base to a vertical surface, and a clamp fixed to each end of said elongate base.

18 Claims, 6 Drawing Sheets

FIRE EXTINGUISHER UNIT

FIELD OF THE INVENTION

The present invention relates to a single-hand fire extinguisher unit that can be releasably mounted to a vertical surface.

BACKGROUND OF THE INVENTION

Rechargeable fire extinguishers have become very common, and often legally required, in most households across the United States. However, rechargeable household fire extinguishers have several shortcomings that prevent or dissuade many individuals from using them effectively.

Rechargeable household fire extinguishers are large and heavy. For example, even the smallest units may weigh more than 5 pounds and are over 16 inches tall. This weight and size makes operation cumbersome, and limits the location in which the fire extinguisher can be mounted. Therefore, it would be desirable to provide a fire extinguisher that is lightweight and compact.

The discharge nozzle on known household fire extinguishers typically requires two steps to operate. First, a safety pin must be removed. Then, a lever actuator must be squeezed. The construction of said discharge nozzle is complicated and intimidating to many individuals. Therefore, it would be desirable to provide a fire extinguisher having a discharge nozzle that is very simple to operate and is un-intimidating in appearance.

SUMMARY OF THE INVENTION

The present invention provides a fire extinguisher that is lightweight and compact, and has a discharge nozzle that is very simple to operate and is un-intimidating in appearance. The fire extinguisher can be operated completely with a single hand. The invention also provides a collapsible holder for releasably supporting the fire extinguisher on a vertical surface.

The fire extinguisher has a cylindrical canister housing, which has a diameter DC, a closed bottom end, and an open neck having a diameter less than DC at the top end. A flexible internal pouch contains the fire suppressant. The flexible pouch is pressurized for expelling the fire suppressant. A valve is connected to the pouch, and is operable between open and closed positions for regulating the flow of fire suppressant from the pouch. A spray head is connected to the valve. The spray head actuates the valve between the closed and open positions and directs the flow of fire suppressant from the pouch. The canister can be grasped with one hand, and the spray head can be depressed with the index finger of the same hand grasping the canister.

In a preferred embodiment, a transparent cap is releasably connected to the neck of the canister. A layer of film envelopes the cap and at least a portion of the canister. The cap can not be removed from the canister without permanently damaging the film layer.

The holder has an elongate base with upper and lower ends. A clamp is fixed to each end of the elongate base. The clamps include a base and a pair of arcuate arms fixed to and extending outwardly transverse to the base. The arcuate arms and base define a socket formed in between the arms. The socket has a diameter less than DC, an open top, and a peripheral slit having a width that is smaller than the diameter of the socket.

The upper and lower clamps are identical in construction except a flange is fixed to at least one of the arms of the lower clamp. The flange extends radially inwardly and defines at least a partial bottom of the socket of the lower clamp.

The arms of at least the first clamp can be resiliently flexed to temporarily widen the width of the slit greater than DC. The fire extinguisher can be parked in the holder by passing the fire extinguisher through the temporarily widened slit of the upper clamp, and then inserting the bottom of the fire extinguisher into the socket of the bottom clamp. The clamps contact the peripheral surface of the canister and support the bottom end of the canister. Alternatively the arms of the bottom clamp may also be resiliently flexed to temporarily widen the width of the slit greater than DC.

Keyholes are provided in the elongate base for mounting the base to a vertical surface. Alternatively, the base may be mounted by releasable fasteners such as magnets, Velcro-type tabs, suction cups, and adhesive strips.

Preferably, the clamps are fixed to the elongate base by releasable connectors. The releasably connectors may comprise a tongue integrally formed at each end of the elongate base and a groove integrally-formed in each clamp. The tongue and groove have shapes that compliment one another.

DETAILED DESCRIPTION OF PREFERRED EMBODIMENTS

For the purpose of illustration, there is shown in the accompanying drawings several embodiments of the invention. However, it should be understood by those of ordinary skill in the art that the invention is not limited to the precise arrangements and instrumentalities shown therein and described below.

Figure 1:
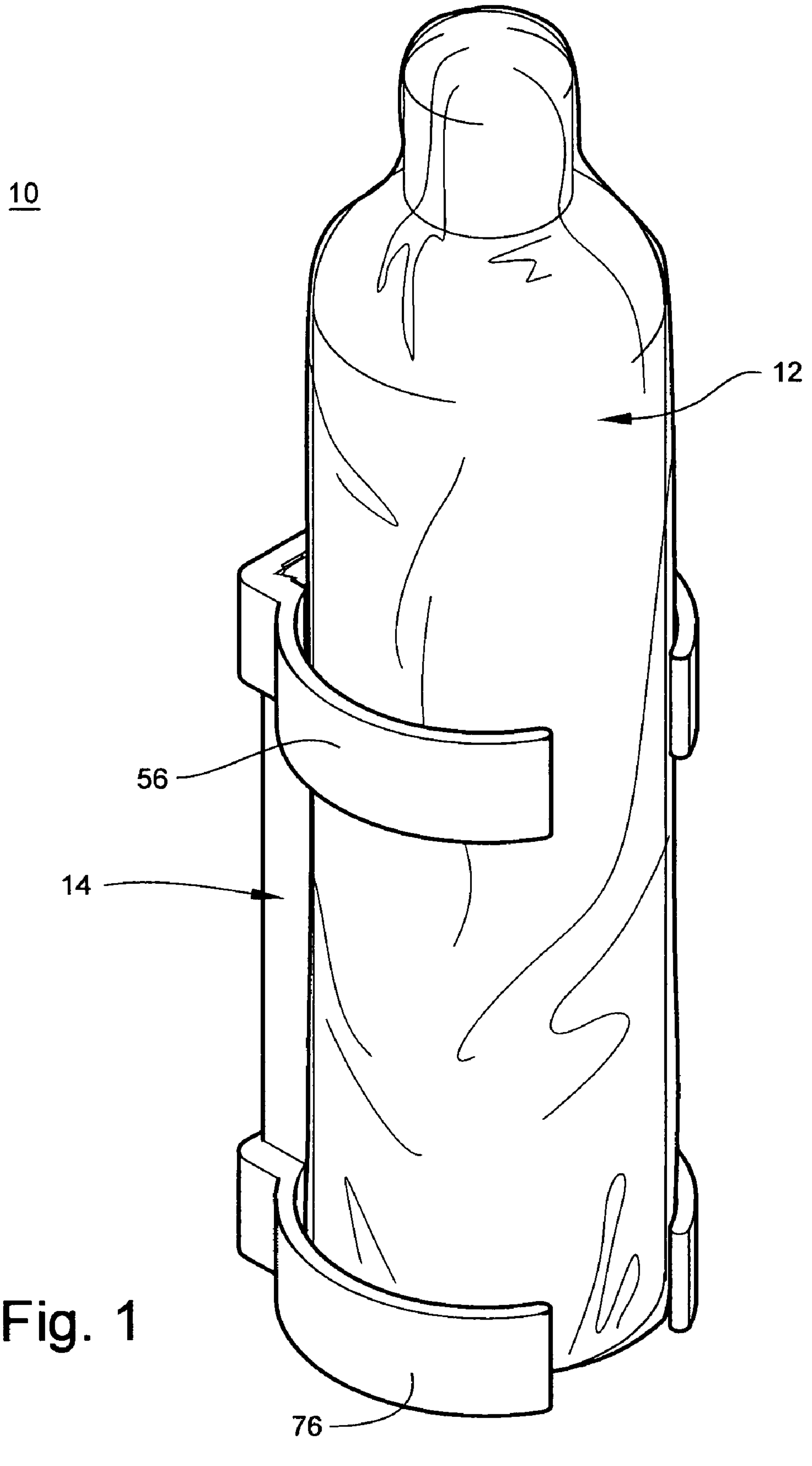
FIG. 1 is an isometric view of a fire extinguisher unit in accordance with an embodiment of the present invention showing the fire extinguisher parked in the holder.

A fire extinguisher unit in accordance with a preferred embodiment of the invention is shown in FIG. 1 and is designated generally by reference numeral 10. The unit 10 generally comprises a fire extinguisher 12 and a holder 14, which can be mounted to a variety of vertical surfaces such as a wall or cabinet. The holder 14 releasably supports the fire extinguisher 12 in a readily accessible location in the event of a fire.

Figure 3:
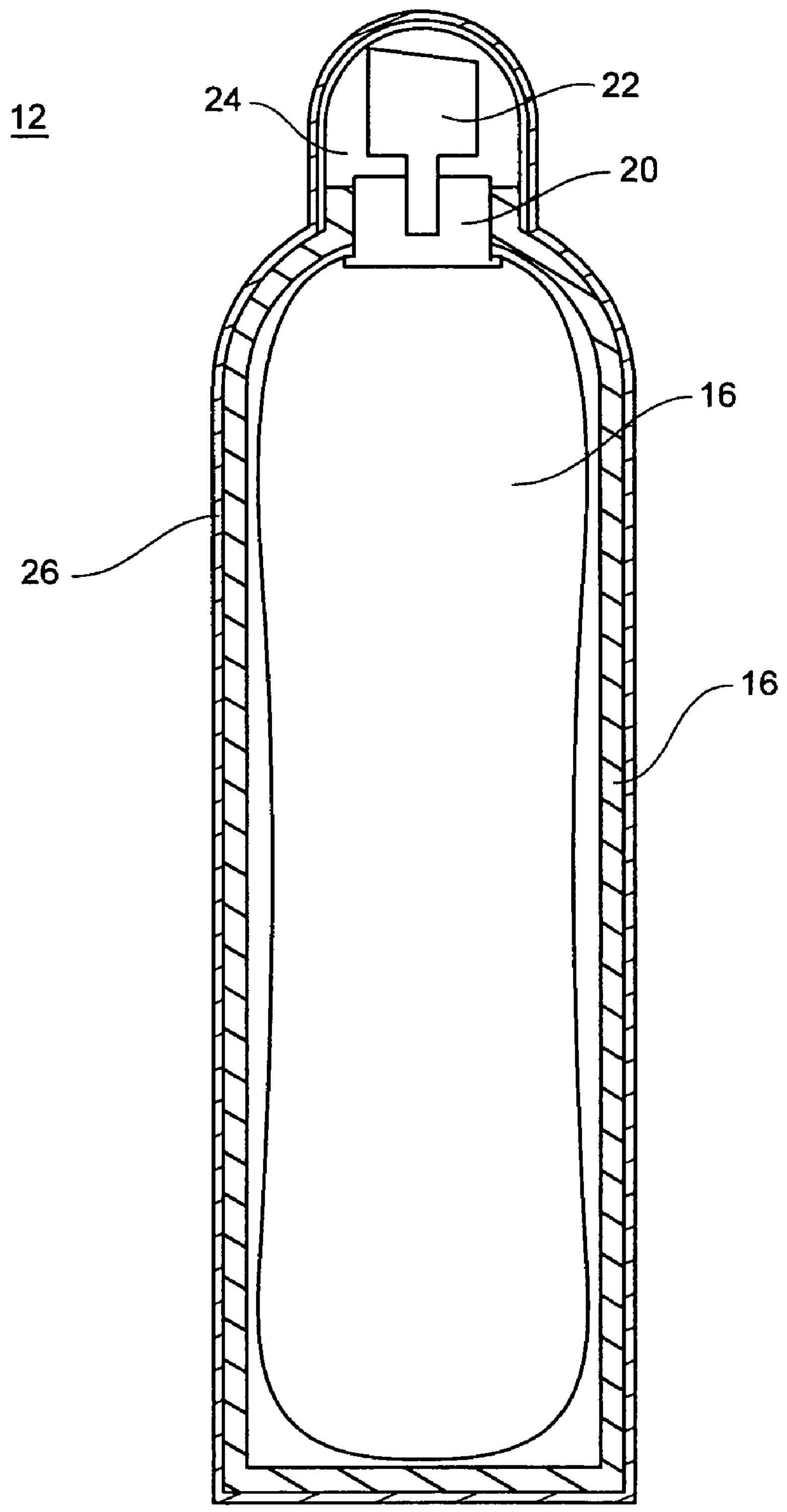
FIG. 3 is a partial cross-sectional view of the fire extinguisher of FIG. 1 showing the canister and flexible bag.

Referring to FIG. 3, the fire extinguisher generally comprises an external metal canister 16, which has a generally-cylindrical shape similar to the shape of a can of hair spray.

The metal canister 16 houses a known nonrechargeable, pressurized spray system, such a disclosed in U.S. Pat. No. 4,969,577, incorporated herein by reference, which includes a flexible bag 18, a valve 20, and a spray head 22. The flexible bag 18 shaped like a pouch having a single, reduced-diameter opening or neck. The bag 18 contains a predetermined quantity of fire suppressant. The bag 18 is externally pressurized by compressed air, which is introduced in between the interior walls of the canister and the outer surface of the bag 18. The valve 20 is connected to the neck of the bag 18. The spray head 22 is connected to the valve 20. The spray head 22 actuates the valve 20 between open and closed positions. The spray head 22 is normally biased upwardly, thereby closing the valve 20. When the spray head 22 is depressed downwardly, it opens the valve 20 and causes fire suppressant to be expelled from the canister 16. The spray head 22 also directs the flow of fire suppressant in the desired direction. As disclosed in U.S. Pat. No. 4,969,577, the valve 20 is constructed so that the force generated by an individual's index finger is sufficient to depress the spray head 22 and open the valve 20.

The canister 16 is preferably made from 18 bar aluminum. The diameter and length of the canister 16 are selected so that the fire extinguisher is lightweight and contains enough fire suppressant to extinguish a small fire. For example, in a preferred embodiment, the fire extinguisher weighs less than about 1.5 pounds, is less than about 3 inches in diameter, and is less than about 12 inches long.

The dimensions of the canister 16 and other components of the fire extinguisher 12 are arranged so that the fire extinguisher 12 can be picked-up and operated with a single hand, i.e., it has a "single-hand" construction. For example, the spray nozzle 22 is constructed so that it can be depressed by an individual's index finger while grasping the canister 16 in a manner similar to spraying a can of paint or hair spray.

A cap 24 snaps on the neck of the canister 16, thereby covering and protecting the spray head 22 from accidental discharge. Similar to known aerosol can caps, the cap 24 is easily removable by grasping the canister 16 with one hand and applying a small upward force on the cap 24 with the other hand. The cap 24 may also be removed by holding the canister 16 with one hand and striking the end of the cap 24 against a rigid surface, such as a table or countertop. Thus, in an emergency situation, the cap 24 can be removed without using the other hand.

In a preferred embodiment, the cap 24 is transparent so that the user can readily see the spray head 22 before the cap 24 is removed. To the user unfamiliar with the fire extinguisher's novel construction, early and immediate visual observation of the spray head 22 reduces the time necessary to decipher the method of operating the fire extinguisher. Further, immediate visual observation of the spray head 22 may also encourage those people with an aversion to or apprehension of fire extinguishers to use the fire extinguisher 12 during the early stages of a fire. Additionally, unobstructed visual observation of the spray head 22 serves to constantly re-educate individuals regarding the simplistic method of operating the novel fire extinguisher 12 of the present invention.

Preferably, a shrink-wrap material 26 envelopes the cap and at least a portion of the canister 16. The shrink-wrap material 26 ensures that the cap 24 is not accidentally removed during shipping. Since the cap can not be removed without damaging the shrink-wrap material 26, the purchaser can ascertain whether the fire extinguisher 12 has been discharged or otherwise tampered with by visually observing the integrity of the shrink-wrap material 26. The shrink-wrap material may comprise known films such as polyvinyl chloride (PVC).

Figure 2:
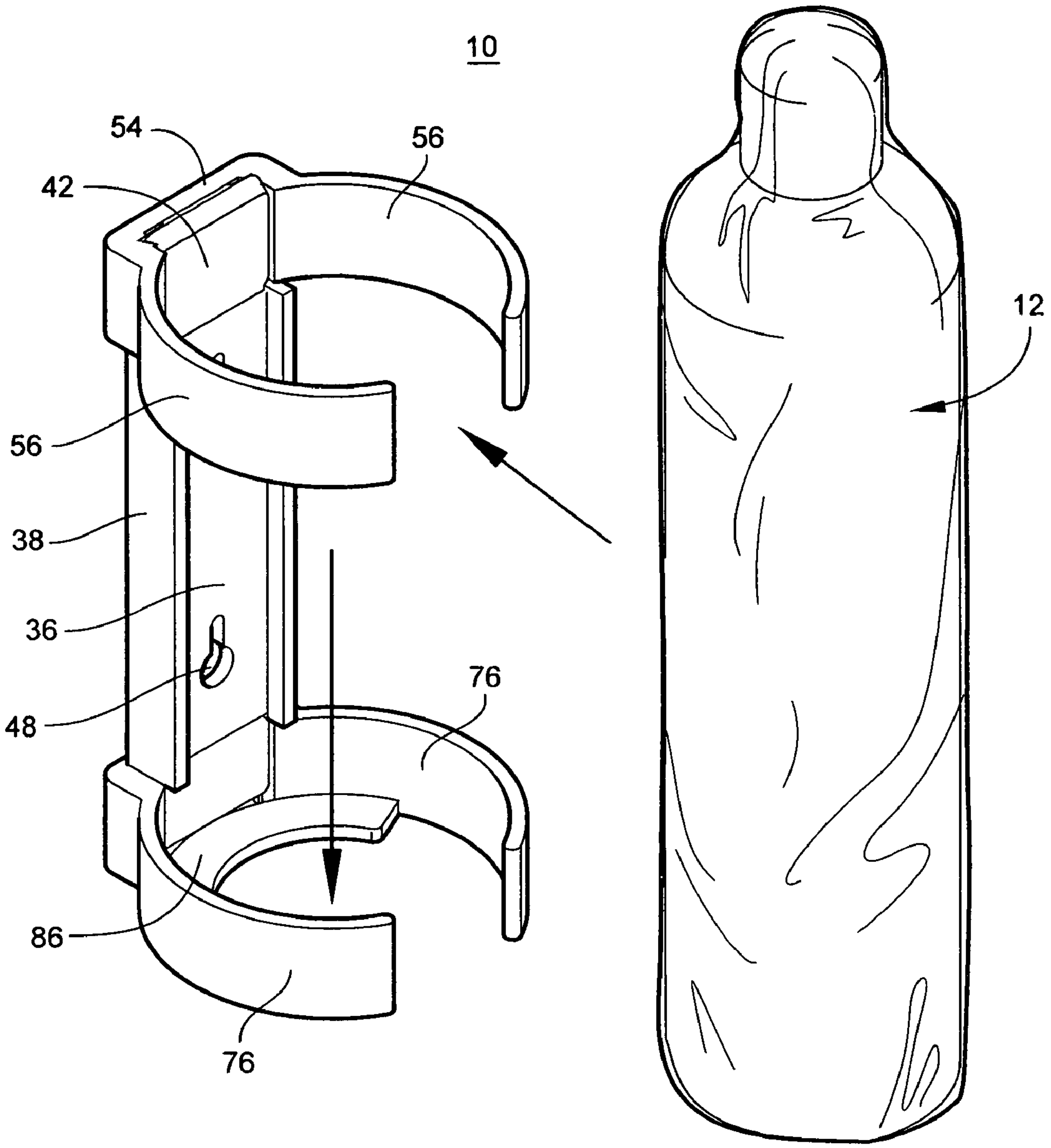
FIG. 2 is an isometric view of the fire extinguisher unit of FIG. 1, showing the method of parking the fire extinguisher in the holder.
Figure 4:
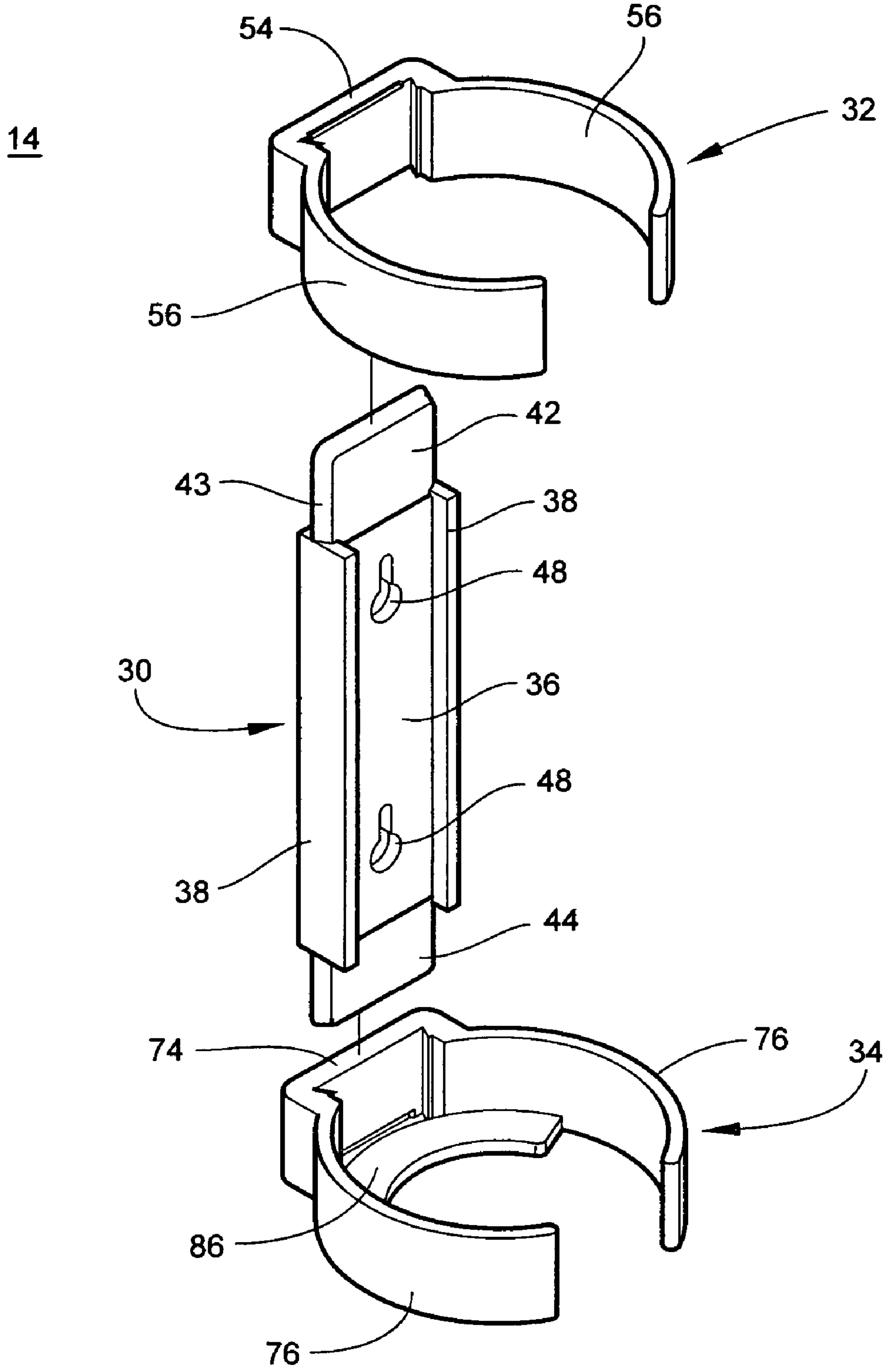
FIG. 4 is an exploded, isometric view of the holder shown in FIGS. 1 and 2.

Referring to FIGS. 2 and 4, the holder 14 generally comprises a holder base 30 and two mounting clamps 32,34. The base 30 and clamps 32,34 include connection means for quickly and easily connecting one clamp 32,34 to each end of the base 30. In a preferred embodiment, the base 30 and clamps 32,34 are formed as separate, interconnecting components so that the holder 14 can be shipped and/or sold in a more compact, disassembled configuration.

As best seen in FIG. 4, the holder base 30 has a generally-rectangular central portion 36. A flange 38 is preferably integrally formed on each lengthwise-extending edge of the central portion 36. The flanges 38 extend perpendicular to the plane of the central portion 36. As seen in FIG. 1, the flanges 38 not only strengthen the base 30, but also cradle the canister 16 when the fire extinguisher 12 is parked in the holder 14.

Figure 5:
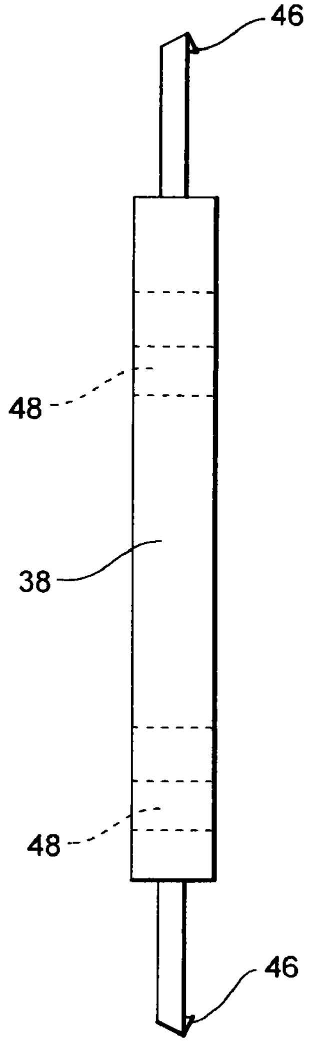
FIG. 5 is a side plan view of the base portion of the holder shown in FIG. 1.

A lengthwise-extending tongue 42,44 is preferably integrally formed on each end of the central portion 36. Referring to FIG. 4, each tongue 42,44 has a tapered edge 43, which compliments the shape of the grooves 60,80 in the clamps 32,34. As best seen in FIG. 5, a protuberance 46 is formed on one side proximate the end of each tongue 42,44. As described below, each tongue 42,44 slidably engages a groove in one of the mounting clamps 32,34.

In one embodiment, a plurality of notched keyholes 48 extends through the central portion 36 of the holder base 30. The keyholes 48 receive the head of a mounting fastener (not shown) such as a nail, toggle bolt, drywall screw, etc. Alternative or additional fasteners may be provided on the back side of the holder 14 such as magnets, Velcro-type fasteners, adhesive strips, and suction cups.

Figure 6:
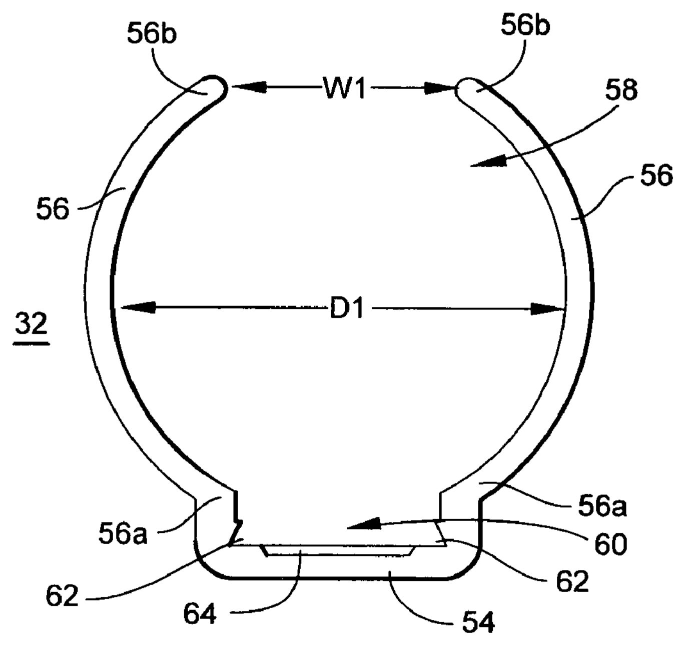
FIG. 6 is a top plan view of the top mounting clamp of the holder shown in FIG. 1.

Referring to FIG. 6., the upper clamp 32 has a base portion 54 and a pair of arcuate arms 56 fixed to opposed ends of the base portion 54. Each arm 56 has a base end 56*a* fixed to the base 54, and a free end 56*b*. The free ends 56*b* are spaced apart a distance W1. In a preferred embodiment, the arms 56 are integrally formed with the base portion 54. The arcuate arms 56 and base portion 54 define a first socket 58. The first socket 58 has a diameter D1, which is preferably slightly smaller than the diameter DC of the canister 16 of the fire extinguisher 12 with which the holder is intended to be used. The socket 58 has an open top, an open bottom, and peripheral slit defined by the free ends 56*b* of the arms 56. The width W1 of the slit is smaller than D1.

Figure 8:
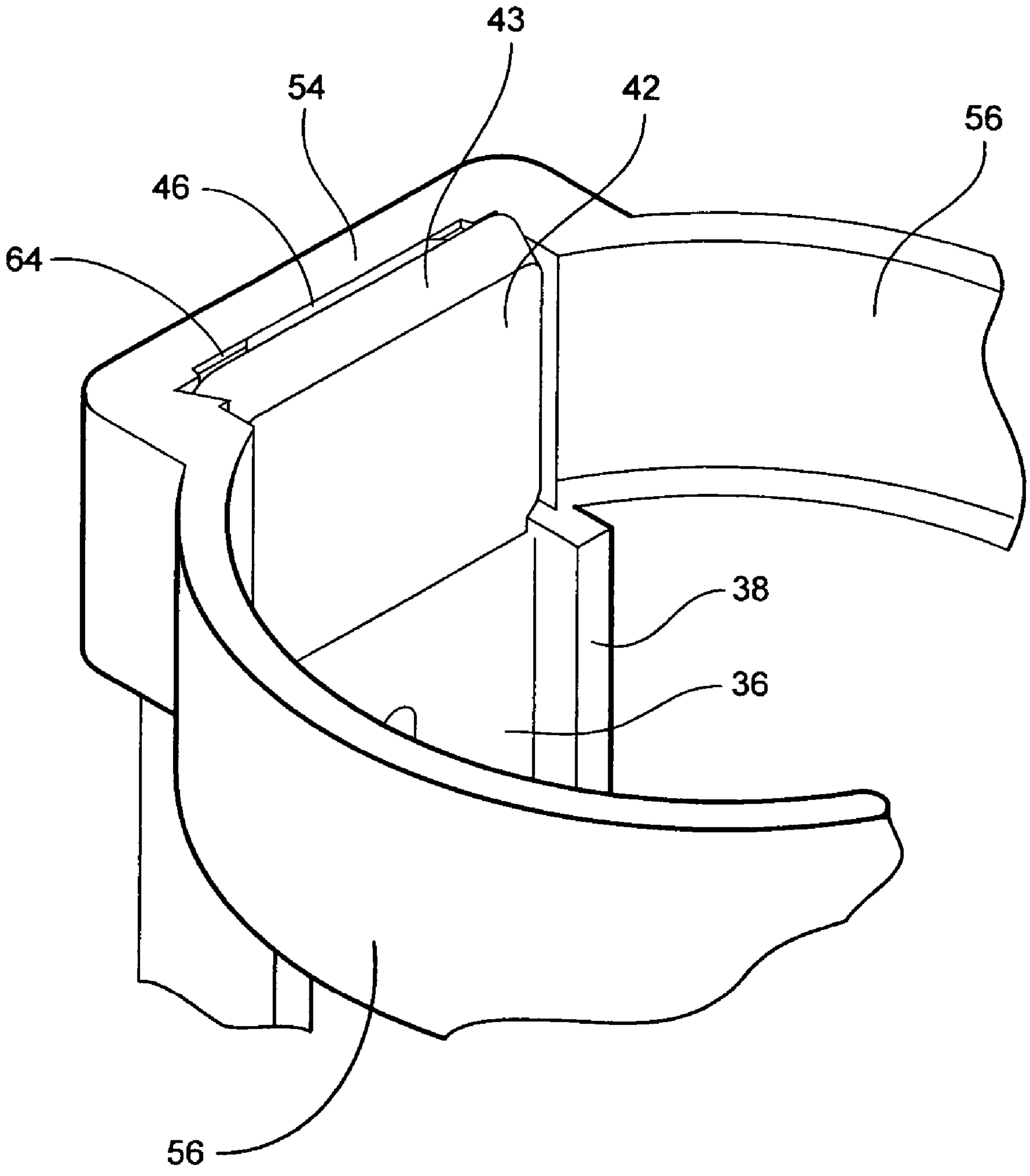

An irregularly-shaped groove 60 is formed in the base portion 50 intermediate the fixed ends 56*a* of the arms 56. Referring to FIGS. 6 and 8, the groove 60 has opposed, angled undercuts 62, which receive the tapered edge 43 of the tongue 42. The groove 60 also has a notch 64, which receives the protuberance 46 and releasably locks the tongue 42 in the groove 60.

Figure 7:
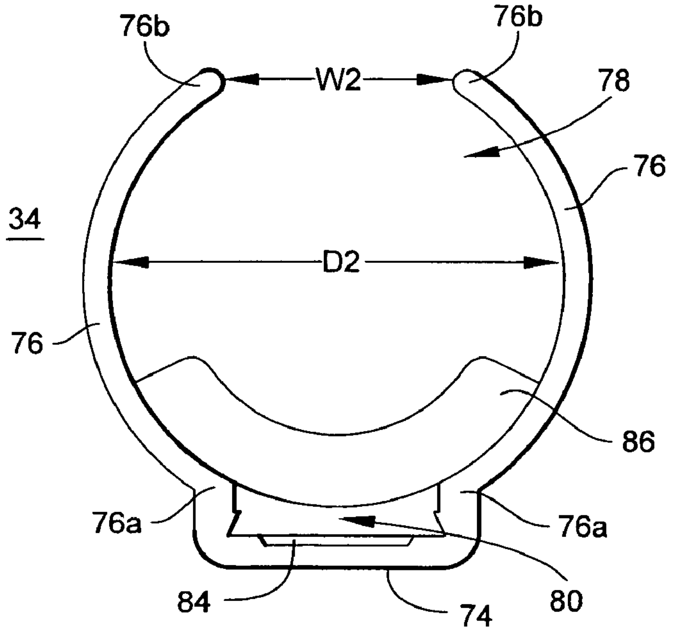
FIG. 7 is a bottom plan view of the bottom mounting clamp of the holder shown in FIG. 1; and, FIG. 8 is an enlarged section of the tongue and groove connection of the holder shown in FIG. 4.

Referring to FIG. 7, the bottom clamp 34 is preferably nearly identical in construction as the top clamp 32. The bottom clamp 34 has a base portion 74 and a pair of arcuate arms 76 fixed to opposed ends of the base portion 74. Each arm 76 has a base end 76*a* fixed to the base portion 74, and a free end 76*b*. The free ends 76*b* are spaced apart a distance W2. In a preferred embodiment, the arms 76 are integrally formed with the base portion 74. The arcuate arms 76 and base portion 74 define a second socket 78. The second socket 78 has a diameter D2, which is preferably slightly smaller than the diameter DC of the canister 16 of the fire extinguisher 12 with which the holder 14 is intended to be used.

The socket 78 has an open top and peripheral slit defined by the free ends 76*b* of the arms 76. The width W2 of the slit is smaller than D2.

Referring to FIG. 7, an irregularly-shaped groove 80 is formed in the base portion 70 intermediate the fixed ends 76*a* of the arms 76. The groove 80 has opposed, angled undercuts 82, which receive the tapered edge 43 of the tongue 42. The groove 80 also has a notch 84, which receives the protuberance 46 and releasably locks the tongue 42 in the groove 80.

Unlike the top clamp 32, the bottom clamp 34 has a flange 86 extending radially-inwardly from the lower edge of at least one of the arcuate arms 76. In the embodiment shown in FIG. 7, the flange 86 is fixed to both arms 76. The flange 86 forms at least a partial socket bottom on which the bottom of the fire extinguisher canister 16 rests.

The thickness of the arms 56 of at least the top clamp is selected to that the arms 56 resiliently flex outwardly, thereby enlarging the width W1 of the slit so that the canister 16 can pass through the slit. The arms 76 of the bottom clamp 34 may also be constructed to resiliently flex outwardly to enlarge the width W2 of the slit. However, in a preferred embodiment, the canister 16 is parked by pushing it through the slit in the top clamp 32 and then lowering the canister 16 into the second socket 78 of the bottom clamp 34 as shown by the directional arrows in FIG. 2. The fire extinguisher 12 can be easily and quickly removed by simply horizontally pulling the canister through the slits of the clamps.

The advantages of a single-hand fire extinguisher are manifest. For example, the extinguisher is small and lightweight enough to be operated by individuals having limited physical strength such as children and the elderly. Additionally, the user can manipulate some other device, such as a telephone, with the individual's free hand.

The construction of the holder is particularly useful for mounting on the wall surface in between a kitchen countertop and the bottom of a cabinet. Cabinets are typically mounted between 16 and 20 inches above the surface of a countertop. Even in this narrow area, the unit 10 described above can be mounted since the fire extinguisher can be parked in the holder 14 without top loading the holder 14. In other words, significant head clearance above the holder 14 is not required to park the fire extinguisher 12 in the holder 14.

While the principles of the invention have been described above in connection with specific embodiments, it is to be clearly understood that this description is made only by way of example and not as a limitation on the scope of the invention.

The invention claimed is:

1. A fire extinguisher unit, comprising:

a) a single-hand fire extinguisher having:

i) a housing comprising a cylindrical canister having a diameter DC, a closed bottom end, and reduced-diameter neck at the top end;

ii) a flexible internal pouch containing fire suppressant;

iii) means for eternally-pressurizing said pouch;

iv) a valve connected to said pouch, said valve being operable between open and closed positions for regulating the flow of fire suppressant from said pouch;

v) a spray head connected to said valve, said spray head actuating said valve between the closed and open positions and directing the flow of fire suppressant from said pouch; and, vi) a transparent cap releasably connected to the neck of said canister, and a layer of film enveloping said cap and at least a portion of said canister, b) a holder, having:

i) an elongate base having first and second ends;

ii) means for mounting said elongate base to a vertical surface; and, iii) a clamp fixed to each end of said elongate base;

wherein said holder releasably supports said fire extinguisher on the vertical surface; and, including a transparent cap releasably connected to the neck of said canister, and a layer of film enveloping said cap and at least a portion of said canister.

2. The fire extinguisher unit recited in claim 1, wherein said canister can be grasped with one hand, and said spray head can be depressed with the index finger of the same hand grasping said canister.

3. The fire extinguisher unit recited in claim 1, wherein said cap can not be removed from said canister without permanently damaging said film layer.

4. The fire extinguisher unit recited in claim 1, wherein said holder clamps the peripheral surface of the canister and supports the bottom end of said canister.

5. A fire extinguisher unit, comprising:

a) a single-hand fire extinguisher having:

i) a housing comprising a cylindrical canister having a diameter DC, a closed bottom end, and reduced-diameter neck at the top end;

ii) a flexible internal pouch containing fire suppressant;

iii) means for externally-pressurizing said pouch;

iv) a valve connected to said pouch, said valve being operable between open and closed positions for regulating the flow of fire suppressant from said pouch;

v) a spray head connected to said valve, said spray head actuating said valve between the closed and open positions and directing the flow of fire suppressant from said pouch;

b) a holder, having:

i) an elongate base having first and second ends;

ii) means for mounting said elongate base to a vertical surface; and, iii) a clamp fixed to each end of said elongate base;

wherein said holder releasably supports said fire extinguisher on the vertical surface;

wherein said clamps are fixed to said elongate base by releasable connectors; and, wherein said releasable connectors comprise a tongue integrally formed at each end of said elongate base and a groove integrally-formed in each clamp, said tongue and groove having shapes that compliment one another.

6. The fire extinguisher unit recited in claim 5, wherein said mounting means is releasable and selected from the group consisting of magnets, Velcro-type tabs, suction cups, and adhesive strips.

7. A fire extinguisher, comprising:

a) a housing comprising a cylindrical canister having a diameter DC, a closed bottom end, and a reduced-diameter neck at the top end;

b) a flexible internal pouch containing fire suppressant;

c) means for pressurizing said pouch;

d) a valve connected to said pouch, said valve being operable between open and closed positions for regulating the flow of fire suppressant from said pouch;

e) a spray head connected to said valve, said spray head actuating said valve between the closed and open positions and directing the flow of fire suppressant from said pouch;

f) a transparent cap covering said spray head and releasably connected to the neck of said canister; and, g) a layer of film enveloping said cap and at least a portion of said canister;

wherein said canister can be grasped with one hand, and said spray head can be linearly depressed with the index finger of the same hand grasping said canister; and, wherein said cap can not be removed from said canister without permanently damaging said film layer.

8. The fire extinguisher recited in claim 7, including a collapsible holder for supporting on a vertical surface a fire extinguisher having a generally cylindrical construction with a diameter DC, comprising:

a) an elongate, generally-planar holder base having an upper end and a lower end, and a tongue fixed to and extending from each end;

b) means for mounting said holder base on the vertical surface;

c) a first clamp removably fixed to and extending transverse to said holder base, said first clamp including:

i) a clamp base;

ii) a groove formed in said clamp base, said groove constructed and arranged to cooperatively engage the top tongue of said holder base; and, iii) a pair of arcuate arms fixed to and extending outwardly transverse to said clamp base, said arcuate arms defining a first socket formed in between said arms, said first socket having a diameter D1 less than DC, an open bottom, an open top, and a peripheral slit having a width W1 that is smaller than D1;

d) a second clamp removably fixed to and extending transverse to said holder base, said second clamp including:

i) a clamp base;

ii) a groove formed in said clamp base, said groove constructed and arranged to cooperatively engage the bottom tongue of said holder base; and, iii) a second pair of arcuate arms fixed to and extending outwardly transverse to said clamp base, said arcuate arms defining a second socket formed in between said arms, said second socket having a diameter D2 that is less than DC and an open top, and;

iv) a flange fixed to at least one of said arms and extending radially inwardly, said flange defining at least a partial bottom of said second socket;

wherein said holder releasably supports the fire-extinguisher on the vertical surface.

9. The holder recited in claim 8, wherein the arms of said first clamp can be resiliently flexed to temporarily widen the width W1 of the slit greater than D1.

10. The holder recited in claim 9, wherein the fire extinguisher can be parked in said holder by passing the fire extinguisher through the temporarily widened slit of said first pair of arcuate arms, and then inserting the bottom of said fire extinguisher into the second socket of said bottom clamp.

11. The holder recited in claim 8, wherein said first clamp is constructed and arranged to contact the annular surface of the cylindrical fire extinguisher and the second clamp supports one end of the fire extinguisher.

12. The holder recited in claim 8, wherein the arms of said second clamp can be resiliently flexed to temporarily widen the width W2 of the slit greater than D2.

13. The holder recited in claim 12, wherein the fire extinguisher can be parked in said holder by passing the fire extinguisher through the temporarily widened slit of said second pair of arcuate arms, and then inserting the bottom of the fire extinguisher into the second socket of said bottom clamp.

14. The holder recited in claim 13, wherein said second clamp is constructed and arranged to contact the annular surface of the cylindrical fire extinguisher and supports one end of the fire extinguisher.

15. The holder recited in claim 8, wherein said mounting means comprises a keyhole extending through said holder base.

16. The fire extinguisher unit recited in claim 8, wherein said mounting means comprises releasable mounting means selected from the group consisting of magnets, Velcro-type tabs, suction cups and adhesive strips.

17. The fire extinguisher recited in claim 7, wherein the diameter of said canister is less than about 3 inches, and the weight of said fire extinguisher is less than about 1.5 pounds.

18. The fire extinguisher recited in claim 7, wherein the fire extinguisher can be operated by removing said cap and depressing said spray head.

* * * * *